United States Patent [19]

Leighton et al.

[11] Patent Number: 4,911,166
[45] Date of Patent: Mar. 27, 1990

[54] PORTABLE LIGHT DELIVERY SYSTEM

[75] Inventors: Stephen B. Leighton, Maplewood, N.J.; Norman E. Rosenthal, Rockville; Thomas A. Wehr, Bethesda, both of Md.

[73] Assignee: The United States of America as represented by the Department of Health and Human Services, Washington, D.C.

[21] Appl. No.: 319,243

[22] Filed: Mar. 6, 1989

Related U.S. Application Data

[63] Continuation-in-part of Ser. No. 167,252, Mar. 11, 1988, and Ser. No. 215,293, Jul. 5, 1988.

[51] Int. Cl.$^4$ .............................................. A61N 5/06
[52] U.S. Cl. ................................. 128/380; 128/396; 362/106
[58] Field of Search ................... 128/395–398, 128/23, 24.1, 303.1; 362/103–106, 32, 107; 353/81; 351/213, 158, 203, 245, 221, 216, 233

[56] References Cited

U.S. PATENT DOCUMENTS

| | | | |
|---|---|---|---|
| 3,621,836 | 11/1971 | Harding et al. | 128/380 |
| 3,883,225 | 5/1975 | Rehm | 351/158 |
| 4,044,756 | 8/1977 | Hamilton et al. | 128/2 |
| 4,057,054 | 11/1977 | Giannone | 351/203 |
| 4,086,004 | 8/1978 | Scrivo et al. | 351/158 |
| 4,145,122 | 3/1979 | Rinard et al. | 351/213 |
| 4,360,253 | 11/1982 | Wyatt | 351/158 |
| 4,553,534 | 11/1985 | Stiegler | 128/24.1 |

FOREIGN PATENT DOCUMENTS 430840 6/1979 U.S.S.R. .............................. 351/213

OTHER PUBLICATIONS

Phillips "Let the Sun Shine In" 12/11/85.

Primary Examiner—Edward M. Coven
Assistant Examiner—Marti S. Graham
Attorney, Agent, or Firm—Glenna Hendricks; Robert L. Price

[57] ABSTRACT

A device for delivering high intensity light to a patient's eyes for treating seasonal affective disorder and the like uses a point source of light such as a high intensity halogen or other incandescent bulb, and directs a large fraction of the light from the bulb directly into the patient's eyes without focusing the light in such a way as to cause damage to the eye or discomfort to the patient. This is accomplished by the use of a positive lens which focuses the light from the high intensity bulb directly in front of the patient's eyes. The light appears to the patient to be coming from an area much larger than the actual point source, and hence is more comfortable for the patient. The patient is assured of receiving a significant dosage of light no matter which way he is directing his gaze.

13 Claims, 1 Drawing Sheet

PORTABLE LIGHT DELIVERY SYSTEM

This is a CIP of parent co-pending applications Serial No. 167,252, filed March 11, 1988, and Serial No. 215,293, filed July 5, 1988, the contents of both of which are hereby incorporated by reference.

FIELD OF INVENTION

The present invention relates to improvements in phototherapy especially in the alleviation of winter depression and similar syndromes; and, more particularly, to an improved device for administering said phototherapy.

BACKGROUND OF THE INVENTION

Reference is made to the aforementioned co-pending applications for the background information.

SUMMARY OF THE INVENTION

The objects of the present invention are the same as those set forth in the aforementioned parent applications, and are hereby respectfully repeated by reference.

Another object of the present invention is to deliver high intensity light to a patient's eyes, for treating seasonal affective disorder and other conditions that may be so treated, and in a manner which is both comfortable to the patient and involves improved efficiency and reduced battery drain.

The present improvement is based on the provision of an improved light delivery system, and desirably utilizes a high intensity halogen or other incandescent bulb as well as means for directing a large fraction of the light from the bulb directly into the patient's eye, without focusing the light in a way that could cause damage to the eye or to the patient. By the proper selection of such a light directing means, including an appropriate means for focusing the beam of light in front of the patient's eye such as a positive or convex lens, preferably of the Fresnel type, the light appears to the patient to be coming from an area much larger than the actual point source, and hence is more comfortable to use. The patient is assured of receiving a significant dosage of light no matter which way he is directing his gaze.

The above and other objects and the nature and advantages of the present invention will be more apparent from the following detailed description of embodiments, taken in conjunction with the drawing wherein:

DETAILED DESCRIPTION OF EMBODIMENTS

In earlier embodiments such as those disclosed in the aforementioned parent co-pending applications, light dosage systems are proposed which use extended fluorescent tubes, or point sources such as incandescent bulbs as sources. Where fluorescent tubes are used as sources, these use more power because the light cannot be focused efficiently, and much of the light is wasted by going in directions other than into the eyes. Where incandescent bulbs are used, the light may not be focused at all or may be focused into a parallel beam of relatively large diameter by the use of a parabolic reflector, such as the type used in flashlights, in which case the light appears to come from only one direction; again, much of the light is wasted and is not directed into the eye. Alternatively, the light may be focused into a small parallel beam by the use of such a parabolic reflector, in which case the light will appear to the patient to be uncomfortably bright.

The present invention uses a focusing means such as a positive lens, preferably of the Fresnel type, to direct the light in a cone toward the eye. The light appears to come from a large source, and so it is not too bright and therefore it is comfortable to the patient. The patient is assured of receiving a significant dosage of light no matter which way he is directing his gaze. The light is efficiently directed into the eye.

Figure 1:
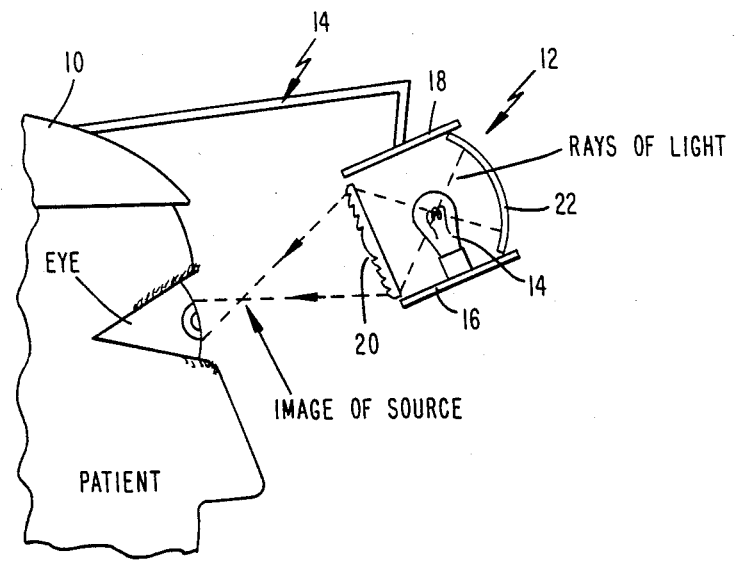
FIG. 1 schematically shows an optical arrangement for a portable light dosage or delivery system according to the present invention.

With reference to FIG. 1, there shown is such a light delivery system including a system supporting means 10 in the form of a helmet, visor, cap, hat or headband such as shown in the aforementioned parent applications. The helmet 10 or the like supports a pair, one for each eye, of optical assemblies 12 through suitable means 14 as schematically illustrated. The optical assemblies 12 are positioned in front of and above the eyes as disclosed in the aforementioned parent applications.

Each assembly 12 contains a point source 14 of light, preferably a small, high efficiency halogen bulb, although any type of incandescent bulb, desirably of the high intensity type, can be used. A suitable housing is provided for the bulb 14, including a bottom support wall 16 for the bulb 14 and its socket, a top wall 18, and preferably a pair of side walls (not shown). Forming the front wall of the housing, or at least a part of the front wall, is a positive (convex) lens 20 of high numerical aperture (desirably at least 0.5* and preferably 0.8* or more), so that such positive lens 20 is placed between the eye and the bulb 14. A concave spherical mirror 22 desirably comprises at least a portion of a rear wall of the housing to redirect light emitted in that direction back toward the lens 20. The spherical mirror 22 is desirably positioned with its center of curvature coincident with the filament of the bulb 14. * This value is unitless, and is obtained by the formula $d/2f$ where d is the diameter of the lens and f is its focal length.

The positioning of the optical elements, and especially the convex lens 20, is very important. Thus, the focal length of the convex lens 20 and its position relative to the bulb 14 and the eye are so chosen that the image of the light source is focused in the front of the eye, e.g. 1-2 cm. in front of the eye. In this way it is ensured that a damaging or uncomfortable concentration of light energy cannot occur within the eye. The light appears to the user to be coming from the entire lens, and hence the light is not unacceptably bright. On the other hand, almost all the light is directed toward the eye so that improved efficiency is obtained adding substantial battery life.

The Fresnel lens 20 and the mirror 22, as well as other parts of the housing, may be formed of lightweight plastic material. If sidewalls are provided for the housing, these may be opaque or translucent, and they may be provided with reflective internal surfaces. The lower and upper walls 18 may also be formed of opaque plastic with reflective inner surfaces.

As disclosed in the parent co-pending applications, the bulb 14 is powered by a suitable battery or battery pack, and appropriate electrical leads are provided along with, if desired, appropriate auxiliary elements as disclosed in parent application Ser. No. 167,252.

Figure 2:
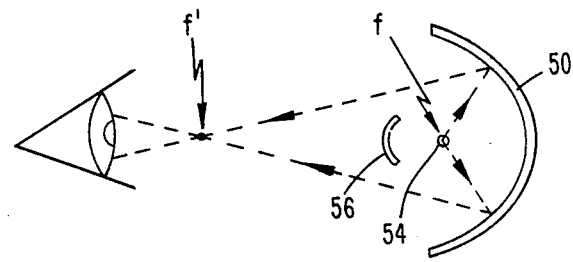
FIGS. 2-4 schematically show alternative embodiments.
Figure 3:
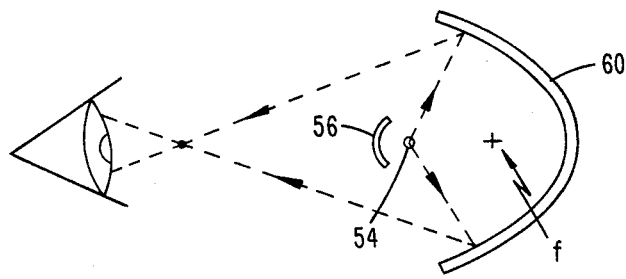
Figure 4:
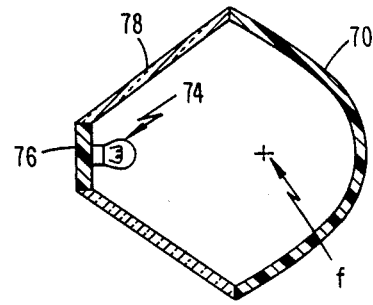

FIGS. 2-4 show additional embodiments which function on the same principle, but which use concave mirrors to focus the beam of light in front of the patient's eye in order to accomplish the same objective as pointed out above.

Of the embodiments of FIGS. 2 and 3 using reflective mirrors instead of a positive lens, that of FIG. 2 is preferred. In this embodiment, the reflective mirror 50 forms part of an ellipse having the focal points f and f'. A high intensity light source 54 is placed at the focal point f. The device is so placed from the eye that the second focal point f' is located in front of the eye, e.g. 1-2 cm. in front of the eye so as to provide the same effect as mentioned above with regard to the description of the FIG. 1 embodiment. To prevent light from the light source 54 going directly to the eye, which would be uncomfortable for the patient, a suitable blocking means 56 is provided, which blocking means may also serve as a support for the high intensity light source 54. The blocking means 56 is preferably a small spherical mirror so that it will reflect light back to the ellipsoidal mirror 50, although the blocking means could be a mirror of another shape or it could be a translucent diffuser or even an opaque block. A small spherical mirror 56 is preferred because it makes most efficient use of the generated light, and it will be understood that the curvature of the spherical mirror should be less than a hemisphere with the light source 54 being desirably at its focal point. In any event, the blocking means 56 should be sufficiently wide so as to shield the light source 54 from direct observation by the patient.

A variation is shown in FIG. 3 wherein the mirror 60 is a paraboloidal mirror or a spherical mirror, especially a spherical mirror approximating an ellipsoid, the mirror 60 having a focal point f. In this case, the location of the light source 54 is not at the focal point f, but instead is closer to the eye than the focal point f. If the light source 54 were placed at the focal point f, then the reflected rays leaving the mirror 60 would be parallel as in a flashlight or an automobile headlamp, and would not focus in front of the eye as required according to the present invention. As in the other embodiments, the elements must be selected so that the light will focus in front of the patient's eyes for the reasons explained above.

FIG. 4 schematically shows a possible structure for effecting the construction of FIGS. 2 and 3, in a form of a sealed-beam lamp similar to a sealed beam headlamp for an automobile, and formed of a single structural unit including an ellipsoidal, spherical or paraboloidal mirror 70 having a focal point f, an incandescent filament 74 serving as a light source and supported on a support and blocking means 76, and an annular transparent portion 78 through which the reflected light is passed so as to focus in front of the eye as shown in FIGS. 2 and 3.

The foregoing description of the specific embodiments will so fully reveal the general nature of the invention that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation.

What is claimed is:

1. A device for shining light into an eye for the treatment of depression comprising:
   support means for mounting said device on the head of a patient;
   light generating means for generating a steady beam of light an intensity of 1,000 to 10,000 lux to the eye, said light generating means being supported by said support means; and
   light projecting means, supported by said support means, for directing said steady beam of light into the eye of the patient, said light projecting means comprising means for focusing said light in the form of a cone from said light generating means immediately in front of the eye of the patient.

2. A device according to claim 1 wherein said means for focusing said light comprises a positive lens.

3. A device according to claim 2 wherein said positive lens is a convex lens.

4. A device according to claim 2 wherein said positive lens is a Fresnel lens.

5. A device in accordance with claim 2 wherein said light projecting means further comprises a spherical mirror disposed behind said light generating means.

6. A device in accordance with claim 1 wherein said light generating means is a high intensity incandescent bulb.

7. A device in accordance with claim 1 wherein said light generating means is a halogen bulb.

8. A device in accordance with claim 1 wherein said means for focusing said light comprises an ellipsoidal mirror, said light generating means being located at a focal point of said ellipsoidal mirror, said ellipsoidal mirror being located relative to the eye such that another focal point of said ellipsoidal mirror is in front of the eye of the patient.

9. A device according to claim 8, further comprising a blocking means located between said light generating means and the eye of the patient.

10. A device in accordance with claim 9 wherein said light blocking means comprises a mirror to direct light back to said ellipsoidal mirror.

11. A device in accordance with claim 1 wherein said means for focusing said light comprises a paraboloidal or spherical mirror having a focal point, said light generating means being located between said focal point and the eye of the patient.

12. A device according to claim 11, further comprising a blocking means located between said light generating means and the eye of the patient.

13. A device in accordance with claim 12 wherein said light blocking means comprises a mirror to direct light back to said paraboloidal or spherical mirror.

* * * * *